United States Patent [19]
Kaiser et al.

[11] Patent Number: 5,874,073
[45] Date of Patent: Feb. 23, 1999

[54] STYLING SHAMPOO COMPOSITIONS CONTAINING AN ODOR MASKING BASE

[75] Inventors: Carl-Eric Kaiser, Cincinnati; Charles Raymond Tremblay, Mason, both of Ohio

[73] Assignee: Procter & Gamble, Cincinnati, Ohio

[21] Appl. No.: 851,321

[22] Filed: May 5, 1997

[51] Int. Cl.$^6$ .............................. A61K 7/07; A61K 7/00
[52] U.S. Cl. ................ 424/70.11; 424/70.1; 424/70.15; 424/70.16; 424/70.17; 514/974
[58] Field of Search .................... 424/70.1, 70.11–70.17; 514/974

[56] References Cited

U.S. PATENT DOCUMENTS

| | | | |
|---|---|---|---|
| 3,679,754 | 7/1972 | Beereboom | 260/587 |
| 4,963,348 | 10/1990 | Bolich, Jr. et al. | 424/71 |
| 5,120,532 | 6/1992 | Wells et al. | 424/70 |
| 5,135,747 | 8/1992 | Faryniarz et al. | 424/401 |
| 5,501,805 | 3/1996 | Behan et al. | 252/8.6 |
| 5,554,588 | 9/1996 | Behan et al. | 512/1 |

*Primary Examiner*—Sally Gardner-Lane
*Attorney, Agent, or Firm*—William J. Winter; David L. Suter; Tara M. Rosnell

[57] ABSTRACT

Disclosed are styling shampoo compositions comprising (a) from about 5% to about 50% by weight of a surfactant component having an anionic moiety at the pH of the composition; (b) from about 0.025% to about 3% by weight of a cationic deposition polymer; (c) from about 0.1% to about 10% by weight of a malodor-producing hair styling polymer; (d) from about 0.0075% to about 2.5% by weight of an odor masking base; and (e) from about 25% to about 94.5% by weight water. The odor masking base comprises (by weight of the base) from about 15% to about 75% by weight of an ionone perfume having a boiling point of more than about 250° C., from about 5% to about 65% by weight of a musk having a boiling point of more than about 250° C., and from about 20% to about 80% by weight of a highly volatile perfume having a boiling point of less than about 250° C. The present invention is also directed to styling shampoo compositions which may further comprise a malodor-producing liquid carrier to solubilize or disperse the malodor-producing polymer in the composition. The odor masking base of the composition helps to mask the malodor of the malodor-producing polymer and/or malodor-producing liquid carrier.

16 Claims, No Drawings

_5,874,073_

STYLING SHAMPOO COMPOSITIONS CONTAINING AN ODOR MASKING BASE

FIELD OF THE INVENTION

The present invention relates to styling shampoo compositions which contain a select combination of perfume materials to mask malodors associated with the use of malodor-producing polymers and/or malodor-producing liquid carriers in the compositions.

BACKGROUND OF THE INVENTION

Personal care products are commercially available in a variety of forms including antiperspirants, deodorants, hand and body lotions, shampoos, liquid and bar soaps, body washes, disposable diapers, and the like. Most of these products contain perfumes which help provide a pleasant fragrance during or after application of the product, or which otherwise help to hide or mask malodors associated with the use of such products.

Many styling shampoo products are never commercialized because it is often too difficult to sufficiently hide or mask malodors associated with the use of such products. Especially problematic are malodors associated with the use of styling shampoo products containing styling polymers, volatile liquid carriers, or combinations thereof. These malodors are even more problematic and difficult to hide or mask with most perfumes when higher concentrations of such malodor-producing polymers and/or malodor-producing liquid carriers are used in the styling shampoo product. These higher concentrations are often necessary to provide improved product benefits such as skin and hair softness, hairstyle, mildness, increased deposition of active ingredients, fragrance longevity, and so forth.

Polymer or liquid carrier malodors, especially those in styling shampoo products, can be made less offensive by using even higher concentrations of perfumes. Although the addition of such higher concentrations of perfumes can alter or reduce the overall offensive character of the polymer or liquid carrier malodors, it often results in an undesirably overbearing perfume odor that is especially offensive when associated with a styling shampoo product. Even when the higher perfume concentrations adequately modify, hide or otherwise mask the polymer or liquid carrier malodors, these higher concentrations do not necessarily result in improved perfume substantivity or longevity, thus resulting in the recurrence of liquid carrier or polymer malodors after the higher perfume concentrations have initially volatilized and no longer have an impact on malodors.

It has now been found that a select combination of perfume materials as defined herein can be incorporated into styling shampoo compositions to effectively reduce the intensity of or mask the malodors associated with the use of malodor-producing polymers, malodor-producing liquid carriers or combinations thereof. This select combination of perfume chemicals comprises a highly volatile perfume, an ionone, and musk.

It is therefore an object of the present invention to provide an odor masking material suitable for use in styling shampoo compositions containing malodor-producing liquid carriers and/or malodor-producing styling polymers, wherein the odor masking material effectively reduces or masks the malodor associated with the use of such compositions. It is a further object of the present invention to provide such an odor masking material which contains a select combination of a highly volatile perfume, an ionone, and musk.

SUMMARY OF THE INVENTION

The present invention is directed to styling shampoo compositions which comprise (a) from about 5% to about 50% by weight of a surfactant component having an anionic moiety at the pH of the composition; (b) from about 0.025% to about 3% by weight of a cationic deposition polymer; (c) from about 0.1% to about 10% by weight of a malodor-producing hair styling polymer; (d) from about 0.0075% to about 2.5% by weight of an odor masking base; and (e) from about 25% to about 94.5% by weight water. The odor masking base comprises (by weight of the base) from about 15% to about 75% by weight of an ionone perfume having a boiling point of more than about 250° C., from about 5% to about 65% by weight of a musk having a boiling point of more than about 250° C., and from about 20% to about 80% by weight of a highly volatile perfume having a boiling point of less than about 250° C. The present invention is also directed to styling shampoo compositions which may further comprise a malodor-producing liquid carrier to solubilize or disperse the malodor-producing polymer in the composition.

It has been found that the select combination of perfume chemicals in the odor masking base effectively helps to mask malodors associated with styling shampoo compositions containing malodor-producing polymers and/or malodor-producing liquid carriers.

DETAILED DESCRIPTION OF THE INVENTION

The styling shampoo compositions of the present invention comprise a malodorous liquid carrier and/or malodorous polymer and an odor masking base to mask or reduce the malodor associated with the use of such malodorous liquid carriers and/or malodorous polymers. The odor masking base is a select combination of ionone perfume, musk, and a highly volatile perfume.

The term "malodor" as used herein refers to any detectable odor associated with a volatile liquid carrier and/or a personal care polymer as recognized by people with normal olfactory acuity.

The term "odor masking base" as used herein refers to a select combination of perfume materials defined herein which are capable of masking or reducing both the odor and scent of malodorous liquid carriers and/or malodorous polymers formulated in styling shampoo compositions.

The term "malodor-producing liquid carrier" as used herein refers to the smell, scent, odor, aroma, or fragrance of volatile liquid carriers as defined herein.

The term "malodor-producing polymer" as used herein refers to the smell, scent, odor, aroma, or fragrance of personal care polymers as defined herein.

The term "soluble" as used herein refers to any material that is sufficiently soluble in a liquid carrier of the styling shampoo composition herein to form a substantially clear solution to the naked eye at a concentration of about 0.2%, preferably at about 0.5%, even more preferably at about 1.0%, by weight of the material in the liquid carrier at 25° C.

The term "insoluble" as used herein refers to any material that is not sufficiently soluble in a liquid carrier of the styling shampoo composition herein to form a substantially clear solution to the naked eye at a concentration of about 0.2%, preferably at about 0.1%, by weight of the insoluble material at 25° C.

The styling shampoo compositions of the present invention can comprise, consist of, or consist essentially of the elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include carriers or by-products that may be included in commercially available materials, unless otherwise specified.

Surfactant Component

The styling shampoo compositions of the present invention comprise a surfactant component to provide cleaning performance to the composition. The surfactant component in turn comprises an anionic surfactant, an amphoteric or zwitterionic surfactant which has an attached group that is anionic at the pH of the composition, or a combination thereof. Such surfactants should be physically and chemically compatible with the essential components described herein, or should not otherwise unduly impair product stability, aesthetics or performance.

Suitable anionic surfactants for use in the styling shampoo composition herein include those which are known for use in hair care or other personal care cleansing compositions. The concentration of the anionic surfactant in the styling shampoo composition should be sufficient to provide the desired cleaning and lather performance, and generally ranges from about 5% to about 50%, preferably from about 6% to about 30%, more preferably from about 7% to about 25%, even more preferably from about 8% to about 18%, by weight of the composition.

Preferred anionic surfactants suitable for use in the styling shampoo compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Specific nonlimiting examples of alkyl ether sulfates which may be used in the styling shampoo compositions of the present invention include sodium and ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic surfactants are the water-soluble salts of organic, sulfuric acid reaction products conforming to the formula $[R^1—SO_3—M]$ where $R^1$ is a straight or branched chain, saturated, aliphatic hydrocarbon radical having from about 8 to about 24, preferably about 10 to about 18, carbon atoms; and M is a cation described hereinbefore. Nonlimiting examples of such surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278, which descriptions are incorporated herein by reference.

Other anionic surfactants suitable for use in the styling shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxyalkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A nonlimiting example of such an alpha-olefin sulfonate mixture is described in U.S. Pat. No. 3,332,880, which description is incorporated herein by reference.

Another class of anionic surfactants suitable for use in the styling shampoo compositions are the beta-alkyloxy alkane sulfonates. These surfactants conform to the formula

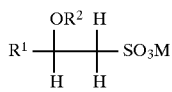

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic surfactants for use in the styling shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Suitable amphoteric or zwitterionic surfactants for use in the styling shampoo composition herein include those which are known for use in hair care or other personal care cleansing compositions, and which contain a group that is anionic at the pH of the shampoo composition. Concentrations of such amphoteric surfactants preferably range from about 0.5% to about 20%, preferably from about 1% to about 10%, by weight of the composition. Nonlimiting examples of suitable zwitterionic or amphoteric surfactants are described in U.S. Pat. Nos. 5,104,646 (Bolich Jr. et al.), 5,106,609 (Bolich Jr. et al.), which descriptions are incorporated herein by reference.

Amphoteric surfactants suitable for use in the styling shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric surfactants for use in the styling shampoo composition of the present invention include cocoamphoacetate, cocoamphodiacetate, lauroamphoacetate, lauroamphodiacetate, and mixtures thereof. Lauroamphoacetate is the most preferred.

Zwitterionic surfactants suitable for use in the styling shampoo composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Nonlimiting examples of suitable zwitterionic surfactants are the betaines including the high alkyl betaines, such as coco dimethyl carboxymethyl betaine, cocoamidopropyl betaine, cocobetaine, lauryl amnidopropyl betaine, oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Most preferred for use herein is cocoamidopropyl betaine.

The styling shampoo compositions of the present invention may further comprise additional surfactants for use in combination with the anionic surfactant component described hereinbefore. Suitable optional surfactants include nonionic surfactants. Any such surfactant known in the art for use in hair or personal care products may be used, provided that the optional additional surfactant is also chemically and physically compatible with the essential components of the styling shampoo composition, or does not otherwise unduly impair product performance, aesthetics or stability. The concentration of the optional additional surfactants in the styling shampoo composition may vary with the cleansing or lather performance desired, the optional surfactant selected, the desired product concentration, the presence of other components in the composition, and other factors well known in the art.

Nonlimiting examples of other anionic, zwitterionic, amphoteric or optional additional surfactants suitable for use in the styling shampoo compositions are described in *McCutcheon's, Emulsifiers and Detergents,* 1989 *Annual,* published by M. C. Publishing Co., and U.S. Pat. Nos. 3,929,678, 2,658,072; 2,438,091; 2,528,378, which descriptions are incorporated herein by reference.

Cationic Deposition Polymer

The styling shampoo compositions of the present invention comprise an organic cationic polymer as a deposition aid for the styling polymer component described hereinafter. Concentrations of the cationic deposition polymer preferably range from about 0.025% to about 3%, more preferably from about 0.05% to about 2%, even more preferably from about 0.1% to about 1%, by weight of the composition.

The cationic deposition polymer, excluding the cationic hair styling polymers described hereinafter, for use in the styling shampoo composition of the present invention contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the styling shampoo composition. The average molecular weight of the cationic deposition polymer is between about 10 million and about 5,000, preferably at least about 100,000, more preferably at least about 200,000, but preferably not more than about 2 million, more preferably not more than about 1.5 million. The polymers also have a cationic charge density ranging from about 0.2 meq/gram to about 5 meq/gram, preferably at least about 0.4 meq/gram, more preferably at least about 0.6 meq/gram, but also preferably less than about 3 meq/gram, more preferably less than about 2 meq/gram, at the pH of intended use of the styling shampoo composition, which pH will generally range from about pH 4 to about pH 9, preferably between about pH 5 and about pH 8.

The charge density can be controlled and adjusted in accordance with techniques well known in the art. As used herein the "charge density" of the cationic polymers is defined as the number of cationic sites per polymer gram atomic weight (molecular weight), and can be expressed in terms of meq/gram of cationic charge. In general, adjustment of the proportions of amine or quaternary ammonium moieties in the polymer, as well as pH of the styling shampoo composition in the case of the amines, will affect the charge density.

Any anionic counterions can be use in association with the cationic deposition polymers so long as the polymers remain soluble in water, in the styling shampoo composition, or in a coacervate phase of the styling shampoo composition, and so long as the counterions are physically and chemically compatible with the essential components of the styling shampoo composition or do not otherwise unduly impair product performance, stability or aesthetics. Nonlimiting examples of such counterions include halides (e.g., chlorine, fluorine, bromine, iodine), sulfate and methylsulfate.

The cationic nitrogen-containing moiety of the cationic deposition polymer is generally present as a substituent on all, or more typically on some, of the monomer units thereof. Thus, the cationic deposition polymer for use in the styling shampoo composition includes homopolymers, copolymers, terpolymers, and so forth, of quaternary ammonium or cationic amine-substituted monomer units, optionally in combination with non-cationic monomers referred to herein as spacer monomers. Nonlimiting examples of such polymers are described in the *CTFA Cosmetic Ingredient Dictionary*, 3rd edition, edited by Estrin, Crosley, and Haynes, (The Cosmetic, Toiletry, and Fragrance Association, Inc., Washington, D.C. (1982)), which description is incorporated herein by reference.

Nonlimiting examples of cationic deposition polymers for use in the styling shampoo composition include polysaccharide polymers, such as cationic cellulose derivatives. Suitable cationic polysaccharide polymers include those which conform to the formula

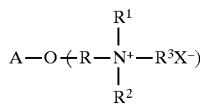

wherein A is an anhydroglucose residual group, such as a cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer JR and LR series of polymers with the most preferred being JR30M and JR400.

Other suitable cationic deposition polymers include cationic guar gum derivatives, such as guar hydroxypropyltrimonium chloride, specific examples of which include the Jaguar series (preferably Jaguar C-17) commercially available from Rhone-Poulenc Incorporated.

The cationic polymers herein are either soluble in the styling shampoo composition, or preferably are soluble in a complex coacervate phase in the styling shampoo composition formed by the cationic deposition polymer and the anionic surfactant component described hereinbefore. Complex coacervates of the cationic deposition polymer can also be formed with other charged materials in the styling shampoo composition.

Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries,* Vol. 106, April 1991, pp 49–54, C. J. van Oss, "Coacervation, Complex-Coacervation and Flocculation", *J. Dispersion Science and Technology,* Vol. 9 (5,6), 1988–89, pp 561–573, and D. J. Burgess, "Practical Analysis of Complex Coacervate Systems", *J. of Colloid and Interface Science,* Vol. 140, No. 1, November 1990, pp 227–238, which descriptions are incorporated herein by reference.

It is believed to be particularly advantageous for the cationic deposition polymer to be present in the styling shampoo composition in a coacervate phase, or to form a coacervate phase upon application or rinsing of the shampoo to or from the hair. Complex coacervates are believed to more readily deposit on the hair which results in improved deposition of the styling polymer. Thus, in general, it is preferred that the cationic deposition polymer exist in the styling shampoo composition as a coacervate phase or form a coacervate phase upon dilution. If not already a coacervate in the styling shampoo composition, the cationic deposition polymer will preferably exist in a complex coacervate form in the shampoo upon dilution with water.

Techniques for analysis of formation of complex coacervates are known in the art. For example, microscopic analyses of the styling shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the styling shampoo composition.

Styling Polymer

The styling shampoo compositions of the present invention comprise a malodor-producing hair styling polymer, preferably a cationic hair styling polymer. Concentrations of the malodor-producing hair styling polymer range from about 0.1% to about 10%, preferably from about 0.2% to about 9%, more preferably from about 0.3% to about 8%, and even more preferably from about 0.3% to about 5%, by weight of the styling shampoo composition.

The malodor-producing hair styling polymers suitable for use in the styling shampoo composition of the present invention include any hair styling polymer known or otherwise effective for providing hair styling performance to a shampoo composition, and which is a malodour-producing polymer as defined herein. The malodor-producing hair styling polymer may be dispersed in the surfactant components described hereinabove, or used in combination with a malodor-producing liquid carrier. The combination of malodor-producing polymer and malodor-producing liquid carrier may result in a malodor that is most easily attributable to the combination rather than to either of the components therein.

The malodor-producing hair styling polymers may be hydrophillic or hydrophobic, water soluble or water insoluble, organic or silicone-containing polymers, some examples of which are disclosed in EPO Application 90307528.1, published as EPO Application 0 408 311 A2 on Jan. 11, 1991, Hayama, et al.; U.S. Pat. Nos. 5,061,481, issued Oct. 29, 1991, Suzuki et al.; 5,106,609, Bolich et al., issued Apr. 21, 1992; 5,100,658, Bolich et al., issued Mar. 31, 1992; 5,100,657, Ansher-Jackson, et al., issued Mar. 31, 1992; 5,104,646, Bolich et al., issued Apr. 14, 1992; U.S. Ser. No. 07/758,319, Bolich et al, filed Aug. 27, 1991, U.S. Ser. No. 07/758,320, Torgerson et al., filed Aug. 27, 1991, which descriptions are incorporated herein by reference.

Preferred malodor-producing hair styling polymers are organic cationic hair styling polymers which have an open chain backbone containing quaternary ammonium or cationic amino moieties, or mixtures thereof. These polymers also have a charge density of less than about 4.75 meq/gram, preferably less than about 3.75 meq/gram, more preferably less than about 3 meq/gram. Furtheremore, the charge density should be of a level such that efficient substantivity between the polymer and the hair can be attained, thereby preventing the hair from becoming unduly coated, sticky, or having an undesirably dirty feel. Preferably, the polymer has a cationic charge density of at least about 1 meq/gram, more preferably at least about 2 meq/gram, at the pH of the shampoo composition.

A nonlimiting example of suitable cationic hair styling polymers include copolymers of vinyl monomers having cationic amine or quaternary ammonium functionalities with water soluble space monomers such as N-vinyl pyrrolidone.

Other suitable cationic hair styling polymers include those cationic polymers containing or derived from quaternary ammonium monomers such as vinyl quaternary ammonium monomers having cyclic cationic nitrogen-containing rings such as imidazolium, e.g., alkyl vinyl imidazolium. The alkyl portions of these monomers are preferably lower alkyls such as the $C_1$–$C_3$ alkyls, more preferably $C_1$ and $C_2$ alkyls.

Preferred malodor-producing hair styling polymers include copolymers of 1-vinyl-2-pyrrolidone and 1-vinyl-3-methylimidazolium salt (e.g., chloride salt) (referred to in the industry as Polyquaternium-16), such as those commercially available from BASF Wyandotte Corp. (Parsippany, N.J., USA) under LUVIQUAT tradename (e.g., LUVIQUAT FC 370, and LUVIQUAT FC 550); t-butyl acrylate/2-ethylhexyl acrylate copolymers having a weight/weight ratio of monomers of about 95/5, about 90/10, about 80/20, about 70/30, about 60/40, and about 50/50; t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl acrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and about 50/50; vinyl pyrrolidone/vinyl acetate copolymers having a weight/weight ratio of monomers of about 10/90, and about 5/95; and mixtures thereof.

Odor Masking Base

The styling shampoo compositions of the present invention comprise an odor masking base which comprises a select combination of a highly volatile perfume, ionone perfume, and musk. Concentrations of the odor making base preferably range from about 0.005% to about 3%, more preferably from about 0.006% to about 2.5%, even more preferably from about 0.0075% to about 1%, by weight of the personal care composition.

The ionones, musks and highly volatile perfumes of the odor masking base are characterized in part by their respective boiling point ranges. The ionone perfumes and musks must have a boiling point under 1 atmosphere of pressure of more than about 250° C., whereas the highly volatile perfumes must have a boiling point under 1 atmosphere of pressure of less than about 250° C.

The boiling point of many perfume materials are disclosed in, e.g., "Perfume and Flavor Chemicals (Aroma Chemicals)," S. Arctander, published by the author, 1969, incorporated herein by reference. Other boiling point values can be obtained from different chemistry handbooks and databases, such as the Beilstein Handbook, Lange's Handbook of Chemistry, and the CRC Handbook of Chemistry and Physics. When a boiling point is given only at a different pressure, usually lower pressure than the normal pressure of one atmosphere, the boiling point at normal or ambient pressure can be approximately estimated by using boiling point-pressure nomographs, such as those given in "The Chemist's Companion," A. J. Gordon and R. A. Ford, John Wiley & Sons Publishers, 1972, pp. 30–36. When applicable, the boiling point values can also be calculated by computer programs, based on molecular structural data, such as those described in "Computer-Assisted Prediction of Normal Boiling Points of Pyrans and Pyrroles," D. T. Stanton et al, J. Chem. Inf. Comput. Sci., 32 (1992), pp. 306–316, "Computer-Assisted Prediction of Normal Boiling Points of Furans, Tetrahydrofurans, and Thiophenes," D. T. Stanton et al, J. Chem. Inf. Comput. Sci., 31 (1992), pp. 301–310, and references cited therein, and "Predicting Physical Properties from Molecular Structure," R. Murugan et al, Chemtech, June 1994, pp. 17–23. All the above publications are incorporated herein by reference.

Each of the ionone perfumes, highly volatile perfumes, and musk components of the odor masking base are described in detail hereinafter.

Highly Volatile Perfume

The highly volatile perfume of the odor masking base comprises perfume materials which compete with the malodorous liquid carrier and/or malodorous polymer molecules to bind to the nasal receptor sites. These highly volatile perfumes are the first odors recognized and identified by the brain, and help inhibit or mask the olfactory recognition of the malodorous liquid carrier and/or malodorous polymer. Concentrations of the highly volatile perfume range from about 15% to about 85%, preferably from about 20% to about 80%, more preferably from about 35% to about 75%, even more preferably from about 45% to about 65%, by weight of the odor masking base.

The highly volatile perfumes are more volatile than the ionone and musk components of the odor masking base, and have a boiling point of less than about 250° C., preferably less than about 230° C., more preferably less than about 220° C. under 1 atmosphere of pressure. These highly volatile perfumes are classified as either aldehydes having from about 2 to about 15 carbon atoms, esters having from about 3 to about 15 carbon atoms, alcohols having from about 4 to about 12 carbon atoms, ethers having from about 4 to about 13 carbon atoms, ketones having from about 3 to about 12 carbon atoms, or combinations thereof.

Nonlimiting examples of suitable aldehydes include n-decyl aldehyde, 10-undecen-1-al, dodecanal, 3,7- dimethyl-7-hydroxyoctan-1-al, 2,4-dimethyl-3-cyclohexene carboxaldehyde, benzaldehyde, anisic aldehyde, and mixtures thereof.

Nonlimiting examples of suitable esters include ethyl acetate, cis-3-hexenyl acetate, 2,6-dimethyl-2,6-octadien-8-yl acetate, benzyl acetate, 1,1-dimethyl-2-phenyl acetate, 2-pentyloxy allyl ester, allyl hexanoate, methyl-2-aminobenzoate, and mixtures thereof.

Nonlimiting examples of suitable alcohols include n-octyl alcohol, beta-gamma-hexenol, 2-trans-6-cis-nonadien-1-ol, 3,7-dimethyl-trans-2,6-octadien-1-ol, 3,7-dimethyl-6-octen-1-ol, 3,7-dimethyl-1,6-octadien-3-ol, 2,6-dimethyl-7-octen-2-ol, 2-phenylethyl alcohol, 2-cis-3,7-dimethyl-2,6-octadien-1-ol, 1-methyl-4-iso-propyl-1-cyclohexen-8-ol, and mixtures thereof.

Nonlimiting examples of suitable ethers include amyl cresol oxide, 4-ethoxy-1-methyl-benzol, 4-methoxy-1-methyl benzene, methyl phenylethyl ether, and mixtures thereof.

Nonlimiting examples of suitable ketones include dimethyl acetophenone, ethyl-n-amyl ketone, 2-heptanone, 2-octanone, 3-methyl-2-(cis-2-penten-1-yl)-2-cyclopenten-1-one, 1-1-methyl-4-iso-propenyl-6-cyclohexen-2-one, para-tertiary-amyl cyclohexanone, and mixtures thereof.

Preferred highly volatile perfumes include 2-pentyloxy allyl ester sold under the tradename Allyl Amyl Glycolate (available from International Flavors and Fragrances, Inc. located in New York, N.Y., U.S.A.); benzaldehyde sold under the tradename Amandol (available from Rhone-Poulenc, Inc located in Princeton, N.J., U.S.A.); cis-3-hexenyl acetate sold under the tradename Verdural extra (available from International Flavors and Fragrances, Inc. located in New York, N.Y., U.S.A.); 2,6-dimethyl-7-octen-2-ol sold under the tradename Dihydromyrcenol (available from International Flavors and Fragrances, Inc. located in New York, N.Y., U.S.A.); para-tertiary-amyl cyclohexanone sold under the tradename Orivone (available from International Flavors and Fragrances, Inc. located in New York, N.Y., U.S.A.); n-decyl aldehyde sold under the tradename Decyl Aldehyde (available from Aceto, Corp. located in Lake Success, N.Y., U.S.A.); and mixtures thereof.

Nonlimiting examples of suitable highly volatile perfumes and their respective boiling point values under 1 atmosphere of pressure include the following:

| Perfume Material | Boiling Point (°C.) |
| --- | --- |
| 3,7-dimethyl-1,6-octadien-3-ol | 198 |
| 3,7-dimethyl-7-hydroxyoctan-1-al | 241 |
| n-decyl aldehyde | 215 |
| benzaldehyde | 179 |
| anisic aldehyde | 248 |
| benzyl acetate | 215 |
| allyl hexanoate | 185 |
| cis-3-hexenyl acetate | 87 |
| methyl-2-aminobenzoate | 237 |
| 2-pentyloxy allyl ester | Flash Point >100 |
| 2-cis-3,7-dimethyl-2,6-octadien-1-ol | 227 |
| 3,7-dimethyl-trans-2,6-octadien-1-ol | 230 |
| 3,7-dimethyl-6-octen-1-ol | 225 |
| 2,6-dimethyl-7-octen-2-ol | 208 |
| 2-phenylethyl alcohol | 220 |
| 1-methyl-4-iso-propyl-1-cyclohexen-8-ol | 219 |
| 1-1-methyl-4-iso-propenyl-6-cyclohexen-2-one | 231 |
| para-tertiary-amyl cyclohexanone | 211 |

Ionone Perfume

The odor masking base comprises an ionone perfume at concentrations ranging from about 15% to about 80%, preferably from about 16% to about 60%, more preferably from about 16% to about 40%, by weight of the odor masking base. These ionone perfumes are a well known class of perfumes chemicals derived from natural oils or manufactured synthetically, which are typically colorless or pale yellow liquids exhibiting woody violet-like odors.

The ionone perfume for use in the odor masking base must have a boiling point under 1 atmosphere of pressure of more than about 250° C., preferably more than about 255° C., even more preferably more than about 260° C., wherein the ionone perfume is preferably selected from methyl ionones, alpha ionones, beta ionones, gamma ionones, or combinations thereof.

Nonlimiting examples of suitable ionones include 1-(2,6,6-Trimethyl-2-cyclohexene-1-yl)-1,6-heptadien-3-one, 2-Allyl-para-menthene-(4(8))-ono-3, Pseudo-allyl-alpha-ionone, alpha-Citrylidene cyclopentanone, 5-(2,6,6-Trimethyl-2-cyclohexen-1-yl)-4-methyl-4-penten-3-one, 6-(2,6,6-Trimethyl-2-cyclohexen-1-yl)-1-methyl-5-hexen-4-one, 2,6,6-Trimethyl cyclohexyl-1-butenone-3, Dihydro-alpha-ionone, 4-(2,6,6-Trimethylcyclohexen-1-yl)-butan-2-one, 4-(2-Methylene-6,6-dimethylcyclohexyl)-butan-2-one, 1-(2,5,6,6-Tetramethyl-2-cyclohexenyl)-butan-3-one, Dihydro-beta-irone, Dihydro-gamma-irone, 5-(2,6,6-Trimethyl-2-cyclohexenyl)-pentan-3-one, Dihydro-iso-methyl-beta-ionone, 6-(2,6,6-Trimethyl-2-cyclohexen-1-yl)-5-hexen-4-one, alpha-Ethyl-2,2,6-trimethyl cyclohexane butyric aldehyde, 4-Methyl-6-(1,1,3-trimethyl-2'-cyclohexen-2'-yl)-3,5-hexadien-2-one, 6,10-Dimethyl undecan-2-one, 6-(2,6,6-Trimethyl-1-cyclohexen-1-yl)-1-methyl-2,5-hexadien-4-one, 6-(2,6,6-Trimethyl-2-cyclohexen-1-yl)-1-methyl-2,5-hexadien-4-one, 4-(2,2,6-Trimethyl-2-cyclohexen-1-yl)-3-buten-2-one, 4-(2,6,6-Trimethyl-1-cyclohexen-1-yl)-3-buten-2-one, 4-(2-Methylene-6,6-dimethylcyclohexyl)-3-buten-2-one, Epoxy-2,3-beta-ionone, Ethyl-2,3-epoxy-3-methyl-5-(2,6,6-trimethyl-2-cyclohexenyl)-4-pentenoate, alpha-ionone methylanthranilate, Methyl-2,3-epoxy-3-methyl-5-(2,6,6-trimethyl-2-cyclohexenyl)-4-pentenoate, 4-(2,5,6,6-Tetramethyl-2-cyclohexen-1-yl)-3-buten-2-one, 6-Methyl-beta-ionone, 6-Methyl-gamma-ionone, 4-(2,6,6-Trimethyl-2-cyclohexenyl)-2,3-dimethyl-2-buten-1-al, 4-(2,6,6-Trimethyl-2-cyclohexen-1-yl)-3-methyl-3-buten-2-one, 5-(2,6,6-Trimethyl-2-cyclohexen-1-yl)-4-penten-3-one, 5-(2,6,6-Trimethyl-1-cyclohexen-1-yl)-4-penten-3-one, 4-(2,6,6-Trimethyl-3-cyclohexen-1-yl)-3-methyl-3-buten-2-one, 5-(2-Methylene-6,6-dimethylcyclohexyl)-4-penten-3-one, 4-(2-Methylene-6,6-dimethylcyclohexyl)-3-methyl-3-buten-2-one, 4-(2,3,6,6-Tetramethyl-2-cyclohexen-1-yl)-3-buten-2-one, 4-(2,4,6,6-Tetramethyl-2-cyclohexen-1-yl)-3-buten-2-one, 4-(2,4,6,6-Tetramethyl-1-cyclohexen-1-yl)-3-buten-2-one, 5-Methyl-1-(3-methyl-3-cyclohexenyl)-1,3-hexanedione, 2-Methyl-4-(2,6,6-trimethyl-2-cyclohexenyl)-3-buten-1-al, 3-Methyl-4-(2,4,6-trimethyl-3-cyclohexenyl)-3-buten-2-one, 4-(2-Methyl-5-iso-propenyl-1-cyclopenten-1-yl)-2-butanone, 4-(2,6,6-Trimethyl-7-cycloheptenyl)-3-buten-2-one, 4-(2,6,6-Trimethyl-4-cyclohexenyl)-3-buten-2-one, 2,6-Dimethylundeca-2,6,8-trien-10-one, 2,6,12-Trimethyl-trideca-2,6,8-trien-10-one, 2,6-Dimethyldodeca-2,6,8-trien-10-one, 2,6,9-Trimethylundeca-2,6,8-trien-10-one, 4-(2,6,6-Trimethyl-2-cyclohexen-1-yl)-3-methyl-3-buten-2-one, 4-(2,4,6-Trimethyl-3-cyclohexen-1-yl)-3-buten-2-one, 5-(2-Methylene-6,6-dimethylcyclohexyl)-4-penten-3-one, and mixtures thereof.

Preferred ionones include 4-(2,6,6-Trimethyl-3-cyclohexen-1-yl)-3-methyl-3-buten-2-one sold under the tradename Isoraldeine (available from Givaudan Roure, Corp. located in Teaneck, N.J., U.S.A.); 5-(2-Methylene-6,6-dimethylcyclohexyl)-4-penten-3-one, sold under the tradename gamma-Methyl Ionone (available from Givaudan Roure, Corp. located in Teaneck, N.J., U.S.A.); 4-(2,2,6-Trimethyl-2-cyclohexen-1-yl)-3-buten-2-one sold under the tradename alpha-Ionone (available from International Flavors and Fragrances, Inc. located in New York, N.Y., U.S.A); 4-(2,6,6-Trimethyl-1-cyclohexen-1-yl)-3-buten-2-one sold under the tradename beta-Ionone (available from International Flavors and Fragrances, Inc. located in New York, N.Y., U.S.A); 4-(2,6,6-Trimethyl-2-cyclohexen-1-yl)-3-methyl-3-buten-2-one sold under the tradename Methyl Ionone (available from Bush Boake Allen, Inc. located in Montvale, N.J., U.S.A.); and mixtures thereof.

Ionones may be incorporated into the odor masking base as one or more individual perfume chemicals or as a specialty perfume containing a combination of perfume chemicals including ionone perfume chemicals. Nonlimiting examples of ionone specialty perfumes include Alvanone Extra available from International Flavors and Fragrances, Inc. located in New York, N.Y., U.S.A., Irisia Base available from Firmenich, Inc. located in Princeton, N.J., U.S.A., Irival available from International Flavors and Fragrances, Inc. located in New York, N.Y., U.S.A., Iritone available from International Flavors and Fragrances, Inc. located in New York, N.Y., U.S.A., and mixtures thereof.

The musk and highly volatile perfumes for use in the odor masking base can also be incorporated into the base as one or more individual perfume chemicals, or as a specialty perfume containing a combination of perfume chemicals. A nonlimiting example of a preferred highly volatile specialty perfume include Cassis Base 345-B available from Firmenich, Inc located in Princeton, N.J., U.S.A.

Nonlimiting examples of suitable ionone perfumes and their respective boiling point values under 1 atmosphere of pressure include the following:

| Perfume Material | Boiling Point (°C.) |
| --- | --- |
| 2,6-Dimethylundeca-2,6,8-trien-10-one | 266 |
| Dihydro-alpha-ionone | 257 |
| 4-(2,6,6-Trimethylcyclohexen-1-yl)-butan-2-one | 253 |
| 4-(2,2,6-Trimethyl-2-cyclohexen-1-yl)-3-buten-2-one | 264 |
| 4-(2,6,6-Trimethyl-1-cyclohexen-1-yl)-3-buten-2-one | 266 |
| 4-(2,5,6,6-Tetramethyl-2-cyclohexen-1-yl)-3-buten-2-one | 286 |
| 5-(2,6,6-Trimethyl-1-cyclohexen-1-yl)-4-penten-3-one | 270 |
| 4-(2,6,6-Trimethyl-2-cyclohexen-1-yl)-3-methyl-3-buten-2-one | 275 |
| 4-(2,4,6-Trimethyl-3-cyclohexen-1-yl)-3-buten-2-one | 276 |
| 5-(2-Methylene-6,6-dimethylcyclohexyl)-4-penten-3-one | 270 |

Musk

The odor masking base comprises a musk component at concentrations of from about 5% to about 70%, preferably from about 15% to about 50%, more preferably from about 20% to about 35%, by weight of the odor masking base. Musk is a well known class of perfumes chemicals that is typically in the form of a colorless or light yellow material having a distinctive, musk-like odor.

The musk component for use in the odor masking base must have a boiling point under 1 atmosphere of pressure of more than about 250° C., preferably more than about 255° C., even more preferably more than about 260° C., wherein the musk component is preferably a polycyclic musk, macrocyclic musk, nitrocyclic musk, or combination thereof, each preferred musk component having more than about 12 carbon atoms, preferably more than about 13 carbon atoms, more preferably more than about 15 carbon atoms.

Suitable polycyclic musks include 5-Acetyl-1,1,2,3,3,6-hexamethylindan, 4-Acetyl-1,1-dimethyl-6-tertiary-butylindan, 7-Acetyl-1,1,3,4,4,6-hexamethyl-1,2,3,4-tetrahydronaphthalene, 1,1,4,4-Tetramethyl-6-ethyl-7-acetyl-1,2,3,4-tetrahydronaphthalene, 1,3,4,6,7,8-Hexahydro-4,6,6,7,8,8-hexamethyl-cyclopenta-gamma-2-benzopyran, and mixtures thereof.

Suitable macrocyclic musks include cyclopentadecanolide, cyclopentadecanolone, cyclopentadecanone, 3-Methyl-1-cyclopentadecanone, cycloheptadecen-9-one-1, cycloheptadecanone, cyclohexadecen-7-olide, cyclohexadecen-9-olide, cyclohexadecanolide, ethylene tridecane dioate, 10-oxahexadecanolide, 11-oxahexadecanolide, 12-oxahexadecanolide, and mixtures thereof.

Suitable nitrocyclic musks include 1,1,3,3,5-Pentamethyl-4,6-dinitroindan, 2,6-Dinitro-3-methoxy-1-methyl-4-tertiary-butylbenzene, 2,6-Dimethyl-3,5-dinitro-4-tertiary-butyl-acetophenone, 2,6-Dinitro-3,4,5-trimethyl-tertiary-butyl-benzene, 2,4,6-Triinitro-1,3-dimethyl-5-tertiary-butylbenzene, and mixtures thereof.

Preferred musks include 1,3,4,6,7,8-Hexahydro-4,6,6,7,8,8-hexamethyl-cyclopenta-gamma-2-benzopyran sold under the tradename Galaxolide (available from International Flavors and Fragrances, Inc. located in New York, N.Y., U.S.A.); cyclopentadecanolide sold under the tradename Exaltolide (available from Firmenich, Inc. located in Princeton, N.J., U.S.A.); ethylene tridecane dioate sold under the tradename Ethylene Brassylate (available from Fragrance Resource, Inc. located in Keyport, N.J., U.S.A.); 7-Acetyl-1,1,3,4,4,6-hexamethyl-1,2,3,4-tetrahydronaphthalene sold under the tradename Tonalid (available from Givaudan Roure, Corp. located in Teaneck, N.J., U.S.A.); and mixtures thereof. Nonlimiting examples of suitable musks and their respective boiling point values under 1 atmosphere of pressure include the following:

| Perfume Material | Boiling Point (°C.) |
| --- | --- |
| 7-Acetyl-1,1,3,4,4,6-hexamethyl-1,2,3,4-tetrahydronaphthalene | 354 |
| ethylene tridecane dioate | 332 |
| 5-Acetyl-1,1,2,3,3,6-hexamethylindan | +300 |
| 1,3,4,6,7,8-Hexahydro-4,6,6,7,8,8,-hexamethyl-cyclopenta-gamma-2-benzopyran (50% IPM) | +250 |
| cyclohexadecen-7-olide | 300 |
| cyclopentadecanolide | 280 |
| cyclohexadecanolide | 294 |
| 2,6-Dinitro-3,4,5-trimethyl-tertiary-butyl-benzene | +250 |

Water

The styling shampoo compositions of the present invention are aqueous liquid carrier systems which comprise from about 25% to about 94.5%, preferably from about 55% to about 85%, more preferably from about 60% to about 75%, of water by weight of the styling shampoo composition.

Optional Components

The styling shampoo compositions of the present invention may further comprise one or more optional components known or otherwise effective for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the styling shampoo compositions.

Nonlimiting examples of optional components for use in the styling shampoo composition include liquid carriers other than water, anti dandruff agents, hair conditioning agents such as hydrocarbon oils, fatty esters, silicones (preferably silicone hair conditioning agents), dyes, pearlescent aids, foam boosters, additional surfactants or non-ionic cosurfactants, pediculocides, pH adjusting agents, preservatives, proteins, skin active agents, sunscreens, vitamins, and viscosity adjusting agents.

The styling shampoo composition of the present invention preferably further comprises a suspending or thickening agent. Suitable suspending agents for such materials are well known in the art, and include crystalline and polymeric suspending or thickening agents. Crystalline suspending agents are preferred, and include known acyl derivatives and amine oxides, and are described in U.S. Pat. No. 4,741,855, which description is incorporated herein by reference.

Non limiting examples of optional polymeric thickening agents for use in the styling shampoo composition include carboxyvinyl polymers, cellulose ethers, guar gum, polyvinyl alcohol, polyvinyl pyrrolidone, hydroxypropyl guar gum, starch and starch derivatives, and xantham gum. Suspending or thickening agents are described in U.S. Pat. Nos. 2,798,053, 4,686,254, 4,788,006, and 5,275,761, which descriptions are incorporated herein by reference. The optional suspending or thickening agents are described in more detail hereinafter.

The styling shampoo composition of the present invention may further comprise a silicone hair conditioning agent, preferably a silicone hair conditioning agent in combination with an optional suspending agent for the silicone. The silicone hair conditioning agent is preferably non volatile, and is preferably present in the styling shampoo composition at concentrations ranging from about 0.01% to about 10% by weight of the styling shampoo composition. Non limiting examples of suitable silicone hair conditioning agents, and optional suspending agents for the silicone, are described in U.S. Reissue Pat. No. 34,584 (Grote et al.), U.S. Pat. Nos. 5,104,646 (Bolich Jr. et al.), 5,106,609 (Bolich Jr. et al.), which descriptions are incorporated herein by reference. The optional silicone hair conditioning agent, and optional suspending agents for the optional silicone, are described in more detail hereinafter.

The styling shampoo composition of the present invention also preferably comprises a malodor-producing liquid carrier to solubilize or disperse the malodor-producing hair styling polymers described hereinbefore. The liquid carrier is included in the styling shampoo composition at concentrations ranging from about 0.10% to about 10% by weight of the styling shampoo composition. Nonlimiting examples of suitable malodor-producing liquid carriers include hydrocarbons, ethers, esters, amines, alkyl alcohols, and volatile silicone derivatives. The optional malodor-producing liquid carrier is described in more detail hereinafter.

Optional Perfume Oil

The styling shampoo compositions of the present invention may further comprise additional perfume chemicals or oils other than those described herein. These optional perfume chemicals or oils are used in addition to and in combination with the odor masking base, to provide the composition with the desired fragrance. Concentrations of the optional perfume chemicals or oils preferably range from about 0.05% to about 5%, more preferably from about 0.06% to about 4.75%, even more preferably from about 0.075% to about 3%, by weight of the composition.

Optional perfume chemicals or oils suitable for use in the styling shampoo composition can be any perfume material, or combination of perfume materials, other than those described hereinbefore and which provide the composition with the desired fragrance. These optional perfume chemicals or oils provide the composition with the desired fragrance, which is substantially unaffected by the malodor of the malodor-producing polymer and/or malodor-producing liquid carrier which is now reduced or masked by the odor masking base.

Preferably the optional perfume oils are used in combination with the odor masking base at a weight ratio of optional perfume oil to odor masking base of from about 50:50 to about 95:5, more preferably from about 55:45 to about 90:10, even more preferably from about 60:40 to about 85:15, most preferably from about 70:30 to about 80:20.

Nonlimiting examples of optional perfume chemicals or oils which are useful in the styling shampoo composition herein are described in *Perfumery and Flavoring Synthetics*, 3rd Revised Edition, Paul Z. Bedoukian, 1986, *Perfume and Flavor Chemicals*, Volumes I and II, Steffen Arctander, 1969, which descriptions are incorporated herein by reference.

Optional Liquid Carrier

The styling shampoo composition of the present invention may further comprise malodor-producing liquid carriers suitable for application to human hair or skin, and which is preferably suitable for solubilizing or dispersing the malodor-producing hair styling polymers described hereinabove. The malodor-producing liquid carrier is included in the styling shampoo composition at concentrations of from about 0.10% to about 10%, preferably from about 0.5% to about 8%, more preferably from about 1% to about 6%, by weight of the styling shampoo composition.

The styling shampoo composition may comprise a combination of the malodor-producing liquid carrier and malodor-producing styling polymer at a weight ratio of malodor-producing styling polymer to malodor-producing liquid carrier of from about 10:90 to about 70:30, preferably from about 20:80 to about 65:35, more preferably from about 30:70 to about 60:40, wherein the combination is associated with a malodor when used in a styling shampoo composition. The malodor associated with such a combination may or may not be easily attributable solely to the malodor-producing liquid carrier or the malodor-producing styling polymer, but rather may be most easily attributable to the combination.

The optional malodor-producing liquid carrier for use in the styling shampoo composition is typically a volatile organic solvent which produces malodors when used in styling shampoo compositions. In this context, the term "volatile" refers to liquid carriers that have a boiling point of less than about 300° C., preferably less than about 260° C., more preferably less than about 200° C. (under 1 atmosphere of pressure). Suitable volatile organic solvents include many liquid carriers which are well known in the chemical arts, for example hydrocarbons, ethers, esters, amines, alkyl alcohols, volatile silicones derivatives, or combinations thereof.

Preferred volatile organic solvents are the hydrocarbon solvents, especially branched chain hydrocarbon solvents. The hydrocarbon solvents may be linear or branched, saturated or unsaturated, hydrocarbons having from about 8 to about 18 carbon atoms, preferably from about 10 to about 16 carbon atoms. Saturated hydrocarbons are preferred, as are branched hydrocarbons. Nonlimiting examples of some suitable linear hydrocarbons include decane, dodecane, decene, tridecene, and combinations thereof. Suitable branched hydrocarbons include isoparaffins, examples of which include commercially available isoparafins from Exxon Chemical Company such as Isopar H and K ($C_{11}$–$C_{12}$ isoparaffins), and Isopar L ($C_{11}$–$C_{13}$ isoparaffins). Preferred branched hydrocarbons are isohexadecane, isododecane, 2,5-dimethyl decane, isotetradecane, and combinations thereof. Commercially available branched hydrocarbons include Permethyl 99A and 101A (available from Preperse, Inc., South Plainfield, N.J., USA).

Suitable ether solvents include di($C_5$–$C_7$) alkyl ethers and diethers, especially di($C_5$–$C_6$) alkyl ethers such as isoamyl ether, dipentyl ether, dihexyl ether, and mixtures thereof.

Suitable ester solvents include $C_5$–$C_{12}$ alkyl esters such as ethyl butyrate, diethyl malonate, diethyl phthalate, diethyl succinate, dimethyl succinate, isopropyl butyrate, and mixtures thereof. Preferred are diethyl phthalate, diethyl malonate, diethyl succinate, dimethyl succinate, and mixtures thereof.

Other suitable volatile organic solvents include isopropanol, butyl alcohol, amyl alcohol, ethanol, benzyl alcohol, phenyl propanol, and mixtures thereof.

Other suitable volatile organic solvents for use in the styling shampoo composition include volatile silicone derivatives such as cyclic or linear polydialkylsiloxane, linear siloxy compounds, or silane compounds. The number of silicon atoms in the cyclic silicones is preferably from about 3 to about 7, more preferably about 3 to about 5.

The general formula for such silicones is:

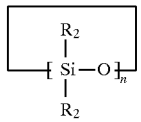

wherein $R_1$ and $R_2$ are independently selected from $C_1$ to $C_8$ alkyl, aryl or alkylaryl and wherein n=3–7. The linear polyorgano siloxanes have from about 2 to 7 silicon atoms and have the general formula:

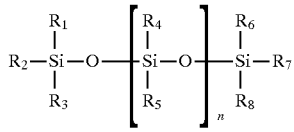

wherein $R_1$, $R_2$, $R_3$, $R_4$, $R_5$, R6, $R_7$ and $R_8$ can independently be saturated or unsaturated $C_1$–$C_8$ alkyl, aryl, alkylaryl, hydroxyalkyl, amino alkyl or alkyl siloxy.

Linear siloxy compounds have the general formula:

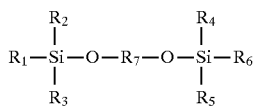

wherein $R_1$, $R_2$, $R_3$, $R_4$, $R_5$, and $R_6$ are independently selected from saturated or unsaturated $C_1$ to $C_7$ alkyl, aryl and alkyl aryl and $R_7$ is $C_1$ to $C_4$ alkylene.

Silane compounds have the general formula:

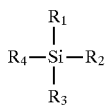

wherein $R_1$, $R_2$, $R_3$, and $R_4$ can independently be selected from $C_1$–$C_8$ alkyl, aryl, alkylaryl, hydroxyalkyl and alkylsiloxy.

Silicones of the above type, both cyclic and linear, are offered by Dow Corning Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes. Examples of volatile silicones are described in Todd and Byers, "Volatile Silicone Fluids for Cosmetics", Cosmetics and Toiletries, Vol. 91, January, 1976, pp. 27–32, and also in Silicon Compounds, pages 253–295, distributed by Petrarch Chemicals, which descriptions are incorporated herein by reference.

Optional Silicone Hair Conditioning Agent

The styling shampoo compositions of the present invention may further comprise an optional silicone hair conditioning agent at concentrations effective to provide hair conditioning benefits. Such concentrations range from about 0.01% to about 10%, preferably from about 0.1% to about 5%, more preferably from about 0.15% to about 3%, most preferably from about 0.2% to about 1%, by weight of the styling shampoo compositions.

The optional silicone hair conditioning agents are insoluble in the styling shampoo compositions, and are preferably nonvolatile. Typically it will be intermixed in the styling shampoo composition so as to be in the form of a separate, discontinuous phase of dispersed, insoluble particles, also referred to as droplets. These droplets are typically suspended with an optional suspending agent described hereinafter. The optional silicone hair conditioning agent phase will comprise a silicone fluid hair conditioning agent such as a silicone fluid and can also comprise other ingredients, such as a silicone resin to improve silicone fluid deposition efficiency or enhance glossiness of the hair (especially when high refractive index (e.g. above about 1.46)) silicone conditioning agents are used (e.g. highly phenylated silicones).

The optional silicone hair conditioning agent phase may comprise volatile silicone, nonvolatile silicone, or combinations thereof. Typically, if volatile silicones are present, it will be incidental to their use as a solvent or carrier for commercially available forms of nonvolatile silicone materials ingredients, such as silicone gums and resins.

The optional silicone hair conditioning agents for use in the styling shampoo compositions preferably have a viscosity of from about 20 to about 2,000,000 centistokes, more preferably from about 1,000 to about 1,800,000 centistokes, even more preferably from about 50,000 to about 1,500,000 centistokes, most preferably from about 100,000 to about 1,500,000 centistokes, as measured at 25° C.

Optional silicone fluids include silicone oils which are flowable silicone materials having a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and combinations thereof. Other insoluble, nonvolatile silicone fluids having hair conditioning properties can also be used.

Optional silicone oils include polyalkyl or polyaryl siloxanes which conform to the following formula (I)

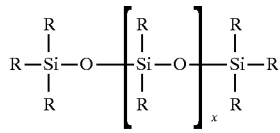

where R is aliphatic, preferably alkyl or alkenyl, or aryl, R can be substituted or unsubstituted, and x is an integer from 1 to about 8,000. Suitable unsubstituted R groups include alkoxy, aryloxy, arylalkyl, arylalkenyl, alkylamine, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the styling shampoo compositions, are chemically stable under normal use and storage conditions, are insoluble in the styling shampoo compositions herein, and are capable of being deposited on and conditioning the hair.

The two R groups on the silicon atom of each monomeric silicone unit may represent the same or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, arylalkyl, and alkylamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and trialkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$-$C(F)_3$, wherein $R^1$ is $C_1$–$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition hereof.

Suitable alkylamino substituted silicones include those which conform to the following structure (II)

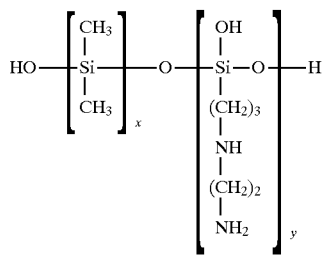

wherein x and y are integers. This polymer is also known as "amodimethicone".

Suitable cationic silicone fluids include those which conform to the formula (III) $(R_1)_a G_{3-a}$-Si-(—$OSiG_2)_n$-(—$OSiG_b(R_1)_{2-b})_m$-O—$SiG_{3-a}(R_1)_a$, wherein G is selected from the group consisting of hydrogen, phenyl, hydroxy, $C_1$–$C_8$ alkyl and preferably methyl; a is 0 or an integer having a value from 1 to 3, preferably 0; b is 0 or 1, preferably 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical conforming to the formula $C_q H_{2q} L$ in which q is an integer having a value of from 2 to 8 and L is selected from the following groups:

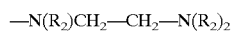

in which $R_2$ is selected from the group consisting of hydrogen, phenyl, benzyl, a saturated hydrocarbon radical, preferably an alkyl radical containing from 1 to 20 carbon atoms, and $A^-$ is a halide ion.

An especially preferred cationic silicone corresponding to formula (III) is the polymer known as "trimethylsilylamodimethicone", of formula (IV):

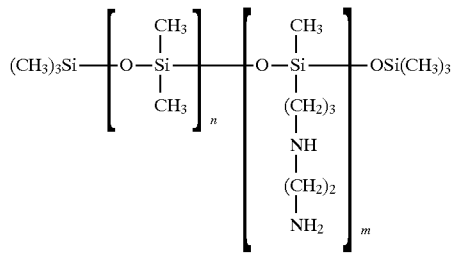

Other silicone cationic polymers which can be used in the styling shampoo compositions are represented by the formula (V):

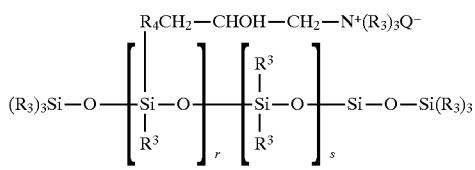

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

Other optional silicone fluids are the insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones,* New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Another category of nonvolatile, insoluble silicone fluid conditioning agents are the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (I) above, as well as cyclic polysiloxanes such as those represented by Formula (VI) below:

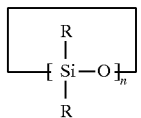

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from faran, imidazole, pyrrole, pyridine, etc. Fused aryl ring substituents include, for example, napthalene, coumarin, and purine.

In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm², typically at least about 27 dynes/cm². Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2NH2$ where each $R^1$ and $R^2$ independently is a $C_1$–$C_3$ alkyl, alkenyl, and/or alkoxy. High refractive index polysiloxanes are available from Dow Corning Corporation (Midland, Mich., U.S.A.) Huls America (Piscataway, N.J., U.S.A.), and General Electric Silicones (Waterford, N.Y., U.S.A.).

References disclosing examples of some suitable silicone fluids for use in the styling shampoo compositions include U.S. Pat. Nos. 2,826,551, 3,964,500, 4,364,837, British Patent 849,433, and Silicon Compounds, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_5$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

Optional Suspending Agent

The styling shampoo compositions of the present invention may further comprise a suspending agent at concentrations effective for suspending the optional silicone hair conditioning agent, or other water-insoluble material, in dispersed form in the styling shampoo compositions. Such concentrations range from about 0.1% to about 10%, preferably from about 0.3% to about 5.0%, by weight of the styling shampoo compositions.

Optional suspending agents include crystalline suspending agents that can be categorized as acyl derivatives, long chain amine oxides, or combinations thereof, concentrations of which range from about 0.1% to about 5.0%, preferably from about 0.5% to about 3.0%, by weight of the styling shampoo compositions. When used in the styling shampoo compositions, these suspending agents are present in crystalline form. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$–$C_{22}$) dimethyl amine oxides, e.g., stearyl dimethyl amine oxide.

Other suitable suspending agents include xanthan gum at concentrations ranging from about 0.3% to about 3%, preferably from about 0.4% to about 1.2%, by weight of the styling shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the styling shampoo compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the styling shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydorxethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Method of Masking

The present invention is also directed to methods of masking or reducing the malodor of styling shampoo compositions containing malodor-producing liquid carriers and/or malodor-producing polymers. Such methods comprise the steps of (a) preparing an odor masking base by combining the following components: (i) from about 20% to about 80% by weight of the base of a highly volatile perfume, (ii) from about 15% to about 75% by weight of the base of an ionone perfume, and (iii) from about 5% to about 65% by weight of the base of a musk component; and (b) mixing the odor masking base of step (a) with the malodor-producing polymer, malodor-producing liquid carrier, or combination thereof, wherein the composition comprises from about 0.005% to about 2.5% by weight of the odor masking base, and from about 0.1% to about 10% by weight of the malodor-producing polymer, malodor-producing liquid carrier, or combination thereof. The methods preferably comprise the preferred composition limitations described hereinbefore.

Method of Use

The styling shampoo compositions of the present invention are used in a conventional manner for cleansing and styling hair. An effective amount of the composition for cleansing and styling the hair is applied to the hair, that has preferably been wetted with water, and is then rinsed off. Such effective amounts preferably range from about 1 gm to about 50 gm, more preferably from about 3 gm to about 20 gm. Application to the hair typically includes working the composition through the hair such that most or all of the hair is contacted with the composition.

This method for cleansing and styling the hair comprises the steps of a) wetting the hair with water, b) applying an effective amount of the styling shampoo composition to the hair, c) shampooing the hair with the composition, and d) rinsing the composition from the hair with water. These steps can be repeated as many times as desired to achieve the cleansing and styling benefit desired. The method is preferably employed daily, every other day, or every third day, to provide and maintain the hair cleansing and styling performance described herein.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. The exemplified embodiments of the styling shampoo composition of the present invention provide masking or reduction of malodorous liquid carriers and/or malodorous polymers contained in the composition. Ingredients are herein identified by chemical, trade, of CTFA name.

The styling shampoo compositions illustrated in Examples IX–XVIII are prepared by conventional formulation and mixing techniques, an example of which is set forth hereinbelow. All exemplified amounts are listed as weight percents and exclude minor materials such as diluents, filler, and so forth, unless otherwise specified.

In the perfume art, some materials having no odor or very faint odor are used as diluents or extenders. Nonlimiting examples of these materials are dipropylene glycol, diethyl phthalate, triethyl citrate, isopropyl myristate, and benzyl benzoate. These materials are used for, e.g., diluting and stabilizing some other perfume materials. These materials are not counted in the formulation of the styling shampoo composition of the present invention.

Preparation

The styling shampoo compositions of the present invention may be prepared using conventional formulation and mixing techniques. The malodor-producing hair styling polymer may be added directly into a surfactant premix or dissolved in the malodor-producing liquid carrier. If the malodor-producing hair styling, polymer is first dissolved in the malodor-producing liquid carrier, this styling polymer/liquid carrier premix may then be added to a premix of the surfactants, or some portion of the surfactants, and the solid components which has been heated to melt the solid components, e.g., about 72° C. This mixture is then pumped through a high shear mill and cooled, and then the remaining components are mixed in. Alternatively, the styling polymer/liquid carrier premix may be added to this final mix, after cooling. The composition should have a final viscosity of from about 2000 to about 15,000 cps, preferably from about 4,000 to about 10,000 cps. The viscosity of the composition can be adjusted using sodium chloride or ammonium xylenesulfonate as needed. The styling polymer/liquid carrier premix, as exemplified hereinbelow, may be a combination of styling polymers/liquid carriers.

An odor masking base may be composed as described in Examples I–VIII. The odor masking base and a perfume oil are then mixed with other ingredients of the composition using conventional formulation and mixing techniques. Odor masking base compositions, as well as perfume blends of the odor masking base and perfume oil, are exemplified in the following examples. The perfume blends can be a combination of odor masking base/perfume oil which is combined with other ingredients of the styling shampoo composition.

| | Odor Masking Base | | | |
|---|---|---|---|---|
| Fragrance Material | I WT % | II WT % | III WT % | IV WT % |
| Allyl Amyl Glycolate[1] | 0.30 | 0.50 | 0.60 | 0.60 |
| Benzaldehyde[2] | 0.20 | 0.40 | 0.40 | 0.40 |
| Cassis 345-B[3] | 1.50 | 2.0 | 3.0 | 3.0 |
| cis-3-Hexenyl acetate[4] | 1.0 | 0.75 | 1.0 | 0.75 |
| Dihydromercenol[5] | 64.50 | 61.85 | 57.0 | 46.65 |
| Orivone[6] | — | 2.0 | 1.0 | 1.0 |
| Irisia Base[7] | 12.0 | — | 10.0 | 8.0 |
| Alvanone Extra[8] | — | — | 2.0 | — |
| n-Decyl aldehyde[9] | 0.50 | 0.50 | 0.50 | 0.60 |
| Tonalid[10] | — | — | — | 10.0 |
| Galaxolide 50 DEP[11] | 15.0 | 18.0 | 21.50 | 20.0 |
| Methyl Ionone[14] | — | 7.0 | — | 1.0 |
| gamma-Methyl Ionone[15] | 5.0 | 7.0 | 3.0 | 8.0 |

[1]- available from International Flavors and Fragrances, Inc.
[2]- available from Rhone-Poulene, Inc. under the tradename Amandol
[3]- speciality perfume material available from Firmenich, Inc.
[4]- available from International Flavors and Fragrances, Inc. under the tradename Verdural extra
[5]- available from International Flavors and Fragrances, Inc.

Odor Masking Base

| Fragrance Material | I WT % | II WT % | III WT % | IV WT % |
|---|---|---|---|---|

[6]- available from International Flavors and Fragrances, Inc.
[7]- speciality perfume material available from Firmenich, Inc.
[8]- speciality perfume material available from International Flavor and Fragrances, Inc.
[9]- available from Aceto, Corp.
[10]- available from Givaudan Roure, Corp.
[11]- available from International Flavors and Fragrances, Inc.
[14]- available from International Flavors and Fragrances, Inc.
[15]- available from International Flavors and Fragrances, Inc.

Odor Masking Base

| Fragrance Material | V WT % | VI WT % | VII WT % | VIII WT % |
|---|---|---|---|---|
| Allyl Amyl Glycolate[1] | 0.75 | 0.40 | 2.0 | 2.0 |
| Benzaldehyde[2] | 0.60 | 0.40 | 1.0 | 1.5 |
| Cassis 345-B[3] | 3.0 | 2.50 | 3.0 | 3.0 |
| cis-3-Hexenyl acetate[4] | 1.0 | 0.75 | 2.0 | 1.5 |
| Dihydromercenol[5] | 58.65 | 61.25 | 36.0 | 11.0 |
| Orivone[6] | 2.0 | 1.0 | — | — |
| Irisia Base[7] | 5.0 | 10.0 | 5.0 | 5.0 |
| Alvanone Extra[8] | 2.0 | 1.0 | — | — |
| n-Decyl aldehyde[9] | 1.0 | 0.70 | 1.0 | 1.0 |
| Tonalid[10] | 5.0 | — | — | 5.0 |
| Galaxolide 50 DEP[11] | 15.0 | 20.0 | 20.0 | 20.0 |
| alpha-Ionone[12] | — | — | 10.0 | 20.0 |
| beta-Ionone[13] | — | — | 10.0 | 10.0 |
| Methyl Ionone[14] | — | — | — | 5.0 |
| gamma-Methyl Ionone[15] | 6.0 | 2.0 | 10.0 | 15.0 |

[1]- available from International Flavors and Fragrances, Inc.
[2]- available from Rhone-Poulene, Inc. under the tradename Amandol
[3]- speciality perfume material available from Firmenich, Inc.
[4]- available from International Flavors and Fragrances, Inc. under the tradename Verdural extra
[5]- available from International Flavors and Fragrances, Inc.
[6]- available from International Flavors and Fragrances, Inc.
[7]- speciality perfume material available from Firmenich, Inc.
[8]- speciality perfume material available from International Flavor and Fragrances, Inc.
[9]- available from Aceto, Corp.
[10]- available from Givaudan Roure, Corp.
[11]- available from International Flavors and Fragrances, Inc.
[12]- available from International Flavors and Fragrances, Inc.
[13]- available from International Flavors and Fragrances, Inc.
[14]- available from International Flavors and Fragrances, Inc.
[15]- available from International Flavors and Fragrances, Inc.

Examples of Perfume Blends of Odor Masking Base and Perfume Oil

| | w/w ratio |
|---|---|
| Perfume Blend A | |
| Odor Masking Base: Example VIII | 50 |
| Perfume Oil | 50 |
| Perfume Blend B | |
| Odor Masking Base: Example VII | 30 |
| Perfume Oil | 70 |
| Perfume Blend C | |
| Odor Masking Base: Example III | 20 |
| Perfume Oil | 80 |
| Perfume Blend D | |
| Odor Masking Base: Example II | 10 |
| Perfume Oil | 90 |

Examples of Styling Polymer and Volatile Liquid Carrier Premix

| | w/w ratio |
|---|---|
| Mixture A. | |
| Styling Polymer: t-butyl acrylate/2-ethylhexyl methacrylate (90/10 w/w) | 40 |
| Liquid carrier: isododecane | 60 |
| Mixture B. | |
| Styling Polymer: vinyl pyrrolidone/vinyl acetate (5/95 w/w) | 50 |
| Liquid carrier: amyl benzoate | 50 |
| Mixture C. | |
| Styling Polymer: vinyl pyrrolidone/vinyl acetate (5/95 w/w) | 50 |
| Liquid carrier: benzyl alcohol | 50 |
| Mixture D. | |
| Styling Polymer: vinyl pyrrolidone/vinyl acetate (5/95 w/w) | 40 |
| Liquid carrier: diethyl succinate | 60 |

Styling Shampoo Compositions

| Component | IX WT % | X WT % | XI WT % | XII WT % | XIII WT % |
|---|---|---|---|---|---|
| Ammonium Laureth Sulfate | 10.5 | 9.5 | 10.0 | 2.0 | 14.0 |
| Ammonium Lauryl Sulfate | 0.5 | — | — | — | — |
| Lauroamphoacetate | 7.0 | — | — | — | — |
| Cocamidopropyl Betaine FB | — | 4.3 | 4.0 | 6.0 | 2.7 |
| Mixture A | 4.0 | — | — | — | — |
| Mixture B | — | 8.0 | — | — | — |
| Mixture C | — | — | 12.0 | — | — |
| Mixture D | — | — | — | 3.0 | 6.0 |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Perfume Blend A | — | — | 1.0 | — | — |
| Perfume Blend B | — | 1.0 | — | — | — |
| Perfume Blend C | 1.0 | — | — | — | 1.0 |
| Perfume Blend D | — | — | — | 1.0 | — |
| Cetyl Alcohol | 0.42 | 0.42 | — | 0.42 | 0.60 |
| Stearyl Alcohol | 0.18 | 0.18 | 0.18 | 0.18 | — |
| PEG-150 Pentaerythrityl Tetrastearate | 0.2 | 0.5 | 0.7 | 0.9 | 1.0 |
| Polyquaternium 10 (JR30M) | — | 0.3 | 0.5 | 0.15 | — |
| Polyquaternium 10 (JR400) | 0.3 | — | — | — | 0.5 |
| Dimethicone | — | 0.3 | 0.3 | — | — |
| DMDM Hydantoin | 0.2 | 0.2 | 0.2 | 0.2 | 0.2 |
| Water | qs 100 | qs 100 | qs 100 | qs 100 | qs 100 |

Styling Shampoo Compositions

| Component | IXV WT % | XV WT % | XVI WT % | XVII WT % | XVIII WT % |
|---|---|---|---|---|---|
| Ammonium Laureth Sulfate | 9.5 | 9.0 | 9.3 | 9.3 | 9.5 |
| Ammonium Lauryl Sulfate | 1.0 | 3.0 | — | — | 1.0 |
| Lauroamphoacetate | 7.5 | 6.0 | — | — | 7.5 |
| Cocamidopropyl Betaine FB[1] | — | — | 4.7 | 4.7 | — |
| Polyquaternium-16 (Luviquat FC 370)[2] | 2.0 | 3.0 | 3.0 | 1.5 | 2.5 |
| Monosodium Phosphate | 0.1 | 0.1 | 0.1 | 0.1 | 0.1 |

Styling Shampoo Compositions

| Component | IXV WT % | XV WT % | XVI WT % | XVII WT % | XVIII WT % |
|---|---|---|---|---|---|
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Perfume Blend A | — | — | 1.0 | — | 1.0 |
| Perfume Blend B | — | 1.0 | — | — | — |
| Perfume Blend C | 1.0 | — | 1.0 | — | — |
| Perfume Blend D | — | — | — | 1.0 | — |
| Cetyl Alcohol | 0.07 | — | 0.42 | 0.42 | 0.14 |
| Stearyl Alcohol | 0.03 | — | 0.18 | 0.18 | 0.06 |
| PEG-150 Pentaerythrityl Tetrastearate | 0.1 | 0.15 | — | 0.08 | 0.20 |
| Polyquaternium 10 (JR30M)[3] | 0.3 | — | 0.3 | — | 0.2 |
| Polyquaternium 10 (JR400)[3] | — | — | — | 0.4 | — |
| Guar Hydroxypropyl-trimonium Chloride (Jaguar C-17)[4] | — | 0.3 | — | — | — |
| Dimethicone | 0.25 | — | — | — | — |
| DMDM Hydantoin | 0.2 | 0.2 | 0.2 | 0.2 | 0.2 |
| Water | qs 100 | qs 100 | qs 100 | qs 100 | qs 100 |

[1]Available from Goldschmidt (Hopewell, Virginia, USA)
[2]Available from BASF (Ludwigshafen, Germany)
[3]Available from Amerchol Corp. (Edison, NJ, USA)
[4]Available from Rhone-Poulenc (Cranbury, NJ, USA)

What is claimed is:

1. A method for masking the malodor of a malodor-producing polymer in styling shampoo compositions, said method comprising the steps of:
   (a) preparing an odor masking base by combining the following components:
      (i) from about 20% to about 80% by weight of the base of a highly volatile perfume having a boiling point of less than about 250° C.,
      (ii) from about 15% to about 75% by weight of the base of an ionone perfume having a boiling point of more than about 250° C., and
      (iii) from about 5% to about 65% by weight of the base of a musk having a boiling point of more than about 250° C.; and
   (b) mixing the odor masking base of step (a) with a malodor-producing polymer selected from the group consisting of Polyquaternium-16 t-butyl acrmlate/2-ethylhexyl acrylate copolymers, t-butyl acrylate/2-ethylhexyl methacrylate copolymers, t-butyl methacrylate/2-ethylhexyl acrylate copolymers, t-butyl methacrylate/2-ethylhexyl methacrylate copolymers, t-butyl ethacrylate/2-ethylhexyl methacrylate copolymers vinyl pyrrolidone/vinyl acetate copolymers, and mixtures thereof
   wherein the composition comprises from about 0.005% to about 2.5% by weight of the odor masking base, and from about 0.1% to about 10% by weight of the malodor-producing polymer.

2. The method of claim 1 wherein the Polyquaternium-16 has a cationic charge density of greater than about 2 meq/gram to less than about 4.75 meq/gram.

3. The method of claim 1 wherein the shampoo composition comprises from about 0.006% to about 1% by weight of the odor masking base.

4. The method of claim 3 wherein the odor masking base comprises from about 16% to about 40% by weight of the ionone perfume, from about 15% to about 50% by weight of the musk, and from about 35% to about 75% by weight of the highly volatile perfume.

5. The method of claim 4 wherein the ionone perfume is selected from the group consisting of methyl ionones, alpha ionones, beta ionones, gamma ionones, and mixtures thereof.

6. The method of claim 4 wherein the musk is selected from the group consisting of polycyclic musks, macrocyclic musks, nitrocyclic musks, and mixtures thereof.

7. The method of claim 4 wherein the highly volatile perfume is selected from the group consisting of aldehydes having from about 2 to about 15 carbon atoms, esters having from about 3 to about 15 carbon atoms, alcohols having from about 4 to about 12 carbon atoms, ethers having from about 4 to about 13 carbon atoms, ketones having from about 3 to about 12 carbon atoms, and mixtures thereof.

8. The method of claim 7 wherein the aldehyde is selected from the group consisting of n-decyl aldehyde, 10-undecen-1-al, dodecanal, 3,7-dimethyl-7-hydroxyoctan-1-al, 2,4-dimethyl-3-cyclohexene carboxaldehyde, benzoic aldehyde, and mixtures thereof.

9. The method of claim 7 wherein the ester is selected from the group consisting of ethyl acetate, cis-3-hexenyl acetate, 2,6-dimethyl-2,6-octadien-8-yl acetate, benzyl acetate, 1,1-dimethyl-2-phenyl acetate, 2-pentyloxy allyl ester, and mixtures thereof.

10. The method of claim 7 wherein the alcohol is selected from the group consisting of n-octyl alcohol, beta-gamma-hexenol, 2-trans-6-cis-nonadien-1-ol, 3,7-dimethyl-trans-2,6-octadien-1-ol, 3,7-dimethyl-6-octen-1-ol, 2,6-dimethyl-7-octen-2-ol, 2-phenylethyl alcohol, and mixtures thereof.

11. The method of claim 7 wherein the ketone is selected from the group consisting of dimethyl acetophenone, ethyl-n-amyl ketone, 2-heptanone, 2-octanone, 3-methyl-2-(cis-2-penten-1-yl)-2-cyclopenten-1-one, 1-1-methyl-4-isopropenyl-6-cyclohexen-2-one, para-tertiary-amyl cyclohexanone, and mixtures thereof.

12. The method of claim 1 wherein the shampoo composition further comprises from about 0.05% to about 5% by weight of a perfume oil, and has a weight ratio of perfume oil to odor masking base of from about 50:50 to about 95:5.

13. The method of claim 1 wherein the shampoo composition further comprises from about 0.10% to about 10% by weight of a malodor-producing liquid carrier selected from the group consisting of hydrocarbons having from about 8 to about 18 carbon atoms, di($C_5$–$C_7$) alkyl ethers and diethers, $C_5$–$C_{12}$ alkyl esters, $C_1$–$C_4$ alcohols, volatile cyclic and linear polydialkylsiloxane, linear siloxy compounds, silane compounds, and mixtures thereof.

14. The method of claim 1 wherein the shampoo composition further comprises a surfactant component selected from the group consisting of ammonium lauryl sulfate, ammonium laureth sulfate, alkyl glyceryl ether sulfonate, lauroamphoacetate, lauroamphodiadetate, cocoamphoacetate, cocoamphodiacetate, betaines, and mixtures thereof.

15. The method of claim 1 wherein the shampoo composition further comprises an organic cationic deposition polymer selected from the group consisting of cationic cellulose polymers, cationic guar gum derivatives, and mixtures thereof having a cationic charge density of from about 0.2 meq/gram to about 2.0 meq/gram.

16. The method of claim 15 wherein the cationic cellulose polymer is Polyquaternium 10.

* * * * *